(12) United States Patent
Nam

(10) Patent No.: US 11,037,290 B2
(45) Date of Patent: Jun. 15, 2021

(54) TOMOGRAPHIC IMAGE PROCESSING DEVICE AND METHOD, AND RECORDING MEDIUM RELATING TO METHOD

(71) Applicant: Samsung Electronics Co., Ltd., Suwon-si (KR)

(72) Inventor: Hyun-jung Nam, Yongin-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 513 days.

(21) Appl. No.: 16/070,577

(22) PCT Filed: Feb. 2, 2017

(86) PCT No.: PCT/KR2017/001098
§ 371 (c)(1),
(2) Date: Jul. 17, 2018

(87) PCT Pub. No.: WO2017/135686
PCT Pub. Date: Aug. 10, 2017

(65) Prior Publication Data
US 2021/0056683 A1   Feb. 25, 2021

(30) Foreign Application Priority Data
Feb. 4, 2016  (KR) .................. 10-2016-0014082

(51) Int. Cl.
*G06T 7/00* (2017.01)
*G06T 11/00* (2006.01)
(Continued)

(52) U.S. Cl.
CPC ............ *G06T 7/0012* (2013.01); *A61B 6/032* (2013.01); *A61B 6/463* (2013.01); *A61B 6/469* (2013.01);
(Continued)

(58) Field of Classification Search
CPC . G06T 2207/10081; G06T 2207/30004; G06T 2207/10072; G06T 2207/10088; G06T 5/008
See application file for complete search history.

(56) References Cited

U.S. PATENT DOCUMENTS 4,839,805 A   6/1989  Pearson, Jr. et al.
5,042,077 A   8/1991  Burke
(Continued)

FOREIGN PATENT DOCUMENTS

CN    1496714      5/2004
CN    101496061    7/2009
(Continued)

OTHER PUBLICATIONS

Korean Notice of Allowance dated Nov. 2, 2017 from Korean Patent Application No. 10-2016-0014082, 7 pages.
(Continued)

*Primary Examiner* — Manuchehr Rahmjoo
(74) *Attorney, Agent, or Firm* — Staas & Halsey LLP

(57) ABSTRACT

A computed tomography (CT) image processing apparatus includes an image processor which sets two or more CT number ranges of interest defined by a window level and a window width for CT numbers of CT image data, and maps the CT numbers to display grayscale values of a display. The display displays the CT image data according to a mapping result. A gradient of a graph showing a relationship between the CT numbers and the display grayscale values in a CT number range included in the two or more CT number ranges of interest, is greater than a gradient in a CT number range not included in the two or more CT number ranges of interest. The graph has a zero or positive gradient over an entire section, or has a zero or negative gradient over the entire section.

15 Claims, 16 Drawing Sheets

(51) Int. Cl.
*G06T 7/11* (2017.01)
*G16H 30/40* (2018.01)
*A61B 6/03* (2006.01)
*A61B 6/00* (2006.01)

(52) U.S. Cl.
CPC .............. *G06T 7/11* (2017.01); *G06T 11/008* (2013.01); *G16H 30/40* (2018.01); *A61B 6/481* (2013.01); *G06T 2200/24* (2013.01); *G06T 2207/10024* (2013.01); *G06T 2207/10081* (2013.01); *G06T 2207/30008* (2013.01)

(56) References Cited

U.S. PATENT DOCUMENTS

| | | |
|---|---|---|
| 5,900,732 A | 5/1999 | Felmlee et al. |
| 6,850,642 B1 | 2/2005 | Wang |
| 7,447,346 B2 | 11/2008 | Sato |
| 8,290,295 B2 | 10/2012 | Criminisi et al. |
| 8,442,290 B2 | 5/2013 | Johnson et al. |
| 9,153,045 B2 | 10/2015 | Polster |
| 9,600,879 B2 | 3/2017 | Bystrov et al. |
| 2004/0057632 A1 | 3/2004 | Gindele |
| 2006/0164524 A1 | 7/2006 | Shibano et al. |
| 2009/0174712 A1 | 7/2009 | De Bliek |
| 2010/0141673 A1* | 6/2010 | Gerade ................. G06T 5/009 345/589 |
| 2010/0226547 A1 | 9/2010 | Criminisi et al. |
| 2014/0005533 A1 | 1/2014 | Grasruck et al. |
| 2015/0287188 A1* | 10/2015 | Gazit ..................... G06T 5/008 382/131 |

FOREIGN PATENT DOCUMENTS

| | | |
|---|---|---|
| CN | 102341825 | 2/2012 |
| CN | 105122301 | 12/2015 |
| JP | 2-210393 | 8/1990 |
| JP | 5-73015 | 3/1993 |
| JP | 2006-61601 | 3/2006 |
| JP | 2009-28431 | 2/2009 |
| JP | 5130002 | 1/2013 |
| KR | 10-2013-0111629 | 10/2013 |

OTHER PUBLICATIONS

International Search Report and Written Opinion of the International Searching Authority dated Apr. 27, 2017 from International Patent Application No. PCT/KR2017/001098, 20 pages.

Extended European Search Report dated Nov. 20, 2018 in corresponding European Patent Application No. 17747731.2.

Chinese Office Action dated Mar. 1, 2021 from Chinese Application No. 201780009890.4, 30 pages.

\* cited by examiner

TOMOGRAPHIC IMAGE PROCESSING DEVICE AND METHOD, AND RECORDING MEDIUM RELATING TO METHOD

CROSS-REFERENCE TO RELATED APPLICATIONS

This application is a National Phase Application under 35 U.S.C. § 371 of PCT International Patent Application No. PCT/KR2017/001098, filed Feb. 2, 2017 which claims the foreign priority benefit under 35 U.S.C. § 119 to Korean Patent Application No. 10-2016-0014082, filed Feb. 4, 2016, the contents of which are incorporated herein by reference.

TECHNICAL FIELD

Disclosed embodiments relate to a tomographic image processing apparatus, a tomographic image processing method, and a computer-readable recording medium storing program code for executing the tomographic image processing method.

BACKGROUND ART

Computed tomography (CT) images may be represented by CT numbers. CT numbers are also referred to as Hounsfield units (HUs), and are values for describing radiolucency. CT numbers may be, for example, integers ranging from about −1024 to 3071, and may be represented as 12-bit image data. CT images are often black-and-white images using CT numbers, or images with limited color components. Accordingly, for accurate diagnosis, images have to be displayed in a wide grayscale range. However, since the number of gray levels that may be displayed on a display may be less than the number of CT numbers of CT image data in some cases, it is difficult to display the CT image data.

DESCRIPTION OF EMBODIMENTS

Technical Problem

The objective of the disclosed embodiments is to enable a user to simultaneously check two or more regions of interest by setting two or more computed tomography (CT) number ranges of interest when a CT image is displayed.

Also, the objective of the disclosed embodiments is to simultaneously check two or more regions of interest without grayscale inversion.

Solution to Problem

According to an aspect of the present disclosure, there is provided a tomographic image processing apparatus including:

an image processor configured to set two or more computed tomography (CT) number ranges of interest defined by a window level and a window width for CT numbers of CT image data, and map the CT numbers to display grayscale values of a display; and the display configured to display the CT image data according to a mapping result, wherein a gradient of a graph showing a relationship between the CT numbers and the display grayscale values in a CT number range included in the two or more CT number ranges of interest is greater than a gradient in a CT number range not included in the two or more CT number ranges of interest, wherein the graph showing the relationship between the CT numbers and the display grayscale values has a zero or positive gradient over an entire section, or has a zero or negative gradient over the entire section.

The tomographic image processing apparatus may further include an input unit configured to receive a user input that designates at least one point of interest in the CT image data, wherein the image processor is further configured to set at least one from among the two or more CT number ranges of interest based on the user input.

The image processor may be further configured to obtain a histogram of the CT numbers of the CT image data, determine a CT number of interest corresponding to a pixel value of a pixel region including a pixel corresponding to the at least one point of interest, and set a CT number range which includes the CT number of interest and has a frequency number equal to or greater than a reference value in the histogram as at least one from among the two or more CT number ranges of interest.

The tomographic image processing apparatus may further include an input unit configured to receive a user input that designates a body part, wherein the image processor is further configured to determine a CT number range corresponding to the body part designated by the user input, and set the determined CT number range as at least one from among the two or more CT number ranges of interest.

The tomographic image processing apparatus may further include an input unit configured to receive a user input that designates a CT number or a CT number range, wherein the image processor is further configured to set at least one from among the two or more CT number ranges of interest based on the CT number or the CT number range designated by the user input.

A ratio of a number of display grayscale values to a number of CT numbers in the two or more CT number ranges of interest may be 1, and a ratio of a number of display grayscale values to a number of CT numbers in the CT number range not included in the two or more CT number ranges of interest may be less than 1.

A number of the CT numbers may be greater than a number of the display grayscale values of the display.

The two or more CT number ranges of interest may include a first CT number range of interest and a second CT number range of interest, wherein the first CT number range of interest has a window level corresponding to a lung, and the second CT number range of interest has a window level corresponding to a bone.

The two or more CT number ranges of interest may include a first CT number range of interest and a second CT number range of interest, wherein the CT image data is CT image data obtained by CT imaging using a contrast agent, wherein the first CT number range of interest has a window level corresponding to cancer tissue that absorbs the contrast agent, and the second CT number range of interest has a window level corresponding to soft tissue.

According to another aspect of disclosed embodiments, there is provided a tomographic image processing method including:

setting two or more computed tomography (CT) number ranges of interest defined by a window level and a window width for CT numbers of CT image data;

mapping the CT numbers to display grayscale values of a display; and displaying the CT image data according to a mapping result, wherein a gradient of a graph showing a relationship between the CT numbers and the display grayscale values in a CT number range included in the two or more CT number ranges of interest is greater than a gradient in a CT number range not included in the two or more CT number ranges of interest, wherein the graph showing the relationship between the CT numbers and the display grayscale values has a zero or positive gradient over an entire section, or has a zero or negative value over the entire section.

The tomographic image processing method may further include: receiving a user input that designates at least one point of interest in the CT image data; and setting at least one from among the two or more CT number ranges of interest based on the user input.

The tomographic image processing method may further include: obtaining a histogram of the CT numbers of the CT image data; determining a CT number of interest corresponding to a pixel value of a pixel region including a pixel corresponding to the at least one point of interest; and setting a CT number range which includes the CT number of interest and that a frequency number equal to or greater than a reference value in the histogram as at least one from among the two or more CT number ranges of interest.

The tomographic image processing method may further include: receiving a user input that designates a body part; determining a CT number range corresponding to the body part designated by the user input; and setting the determined CT number range as at least one from among the two or more CT number ranges of interest.

The tomographic image processing method may further include: receiving a user input that designates a CT number or a CT number range; and setting at least one from among the two or more CT number ranges of interest, based on the CT number or the CT number range designated by the user input.

A ratio of a number of display grayscale values to a number of CT numbers in the two or more CT number ranges of interest may be 1, and a ratio of a number of display grayscale values to a number of CT numbers in the CT number range not included in the two or more CT number ranges of interest may be less than 1.

A number of the CT numbers may be greater than a number of the display grayscale values of the display.

The two or more CT number ranges of interest may include a first CT number range of interest and a second CT number range of interest, wherein the first CT number range of interest has a window level corresponding to a lung, and the second CT number range of interest has a window level corresponding to a bone.

The two or more CT number ranges of interest may include a first CT number range of interest and a second CT number range of interest, wherein the CT image data is CT image data obtained by CT imaging using a contrast agent, wherein the first CT number range of interest has a window level corresponding to cancer tissue that absorbs the contrast agent, and the second CT number range of interest has a window level corresponding to soft tissue.

According to another aspect of disclosed embodiments, there is provided a computer-readable recording medium storing program code for executing the tomographic image processing method.

Advantageous Effects of Disclosure

According to disclosed embodiments, a user may simultaneously check two or more regions of interest by setting two or more computed tomography (CT) number ranges of interest when a CT image is displayed.

Also, according to disclosed embodiments, two or more regions of interest may be simultaneously checked without grayscale inversion.

BEST MODE

Figure 1:
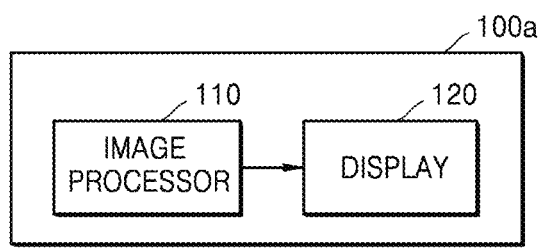
FIG. 1 is a block diagram illustrating a structure of a tomographic image processing apparatus 100a according to an embodiment.

According to an aspect of embodiments, a computed tomography (CT) image processing apparatus includes: an image processor configured to set two or more computed tomography (CT) number ranges of interest defined by a window level and a window width for CT numbers of CT image data, and map the CT numbers to display grayscale values of a display; and the display configured to display the CT image data according to a mapping result, wherein a gradient of a graph showing a relationship between the CT numbers and the display grayscale values in a CT number range included in the two or more CT number ranges of interest is greater than a gradient in a CT number range not included in the two or more CT number ranges of interest, wherein the graph showing the relationship between the CT numbers and the display grayscale values has a zero or positive gradient over an entire section, or has a zero or negative gradient over the entire section.

MODE OF DISCLOSURE

Advantages and features of the present disclosure and methods of accomplishing the same may be understood more readily by reference to the following detailed description of embodiments and the accompanying drawings. However, the present embodiments may have different forms and should not be construed as being limited to the descriptions set forth herein. Rather, these embodiments are provided so that this disclosure will be thorough and complete and will fully convey the scope of the present disclosure to one of ordinary skill in the art, and the present disclosure will only be defined by the appended claims. Like reference numerals refer to like elements throughout the specification.

The terms used in the present disclosure are selected from among common terms that are currently widely used in consideration of their functions in the present disclosure. However, the terms may be different according to an intention of one of ordinary skill in the art, a precedent, or the advent of new technology. Also, in particular cases, the terms are discretionally selected by the applicant of the present disclosure, and the meaning of those terms will be described in detail in the corresponding part of the detailed description. Therefore, the terms used in the present disclosure are not merely designations of the terms, but the terms are defined based on the meaning of the terms and content throughout the present disclosure.

When a part "includes" or "comprises" an element, unless there is a particular description contrary thereto, the part may further include other elements, not excluding the other elements. Also, the term "unit" in the embodiments means a software component or a hardware component such as a field-programmable gate array (FPGA) or an application-specific integrated circuit (ASIC), and performs a specific function. However, the term "unit" is not limited to software or hardware. The "unit" may be formed so as to be in an addressable storage medium, or may be formed so as to operate one or more processors. Thus, for example, the term "unit" may include any one or more of components such as software components, object-oriented software components, class components, and task components, processes, functions, attributes, procedures, subroutines, segments of program code, drivers, firmware, micro codes, circuits, data, a database, data structures, tables, arrays, and variables. Functions provided by the components and "units" may be combined into a smaller number of components and "units", or may be divided into additional components and "units".

Hereinafter, embodiments of the present disclosure will be described in detail with reference to the accompanying drawings in order to enable one of ordinary skill in the art to easily embody and practice the present disclosure. However, the present disclosure is not limited to examples disclosed below, but may be implemented in various forms. Also, parts in the drawings unrelated to the detailed description are omitted to ensure clarity of the present disclosure.

Throughout the specification, an "image" may mean multi-dimensional data formed of discrete image elements, e.g., pixels in a two-dimensional (2D) image and voxels in a three-dimensional (3D) image. For example, the image may include a medical image of an object which is captured by a computed tomography (CT) imaging apparatus.

Throughout the specification, a "CT image" may mean an image generated by synthesizing a plurality of X-ray images that are obtained by imaging an object while a CT imaging apparatus rotates around at least one axis with respect to the object.

Throughout the specification, an "object" may be a human, an animal, or a portion of a human or an animal. For example, the object may include at least one of an organ (e.g., the liver, heart, womb, brain, breast, or abdomen), and a blood vessel. Also, the object may be a phantom. The phantom means a material having a density, an effective atomic number, and a volume that are approximately the same as those of an organism. For example, the phantom may be a spherical phantom having properties similar to a physical body.

Throughout the specification, a "user" may be, but is not limited to, a medical expert including a medical doctor, a nurse, a medical laboratory technologist, a medical imaging specialist, or a technician who repairs a medical apparatus.

Since a CT system is capable of providing a cross-sectional image of an object, the CT system may distinctively express an inner structure, e.g., an organ such as a kidney or a lung, of the object, compared to a general X-ray imaging apparatus.

The CT system may obtain a plurality of pieces of image data with a thickness not more than 2 mm several hundred times per second and then may process the plurality of pieces of image data, so that the CT system may provide a relatively accurate cross-sectional image of the object. According to the related art, only a horizontal cross-sectional image of the object may be obtained, but this issue has been overcome due to various image reconstruction methods. Examples of 3D image reconstruction methods are as follows.

Shade surface display (SSD)—an initial 3D imaging method of displaying only voxels having a predetermined Hounsfield Units (HU) value.

Maximum intensity projection (MIP)/minimum intensity projection (MinIP)—a 3D imaging method of displaying only voxels having the greatest or smallest HU value from among voxels that construct an image.

Volume rendering (VR)—an imaging method capable of adjusting a color and a transmittance of voxels that constitute an image, according to regions of interest.

Virtual endoscopy—a method that allows endoscopy observation in a 3D image that is reconstructed by using the VR method or the SSD method.

Multi-planar reformation (MPR)—a method of reconstructing an image into a different cross-sectional image. A user may reconstruct an image in any desired direction.

Editing—a method of editing adjacent voxels so as to allow a user to easily observe a region of interest in volume rendering.

Voxel of interest (VOI)—a method of displaying only a selected area in volume rendering.

A tomographic image processing apparatus according to disclosed embodiments may be implemented as a CT system. Also, the tomographic image processing apparatus according to disclosed embodiments may be implemented as an electronic apparatus including a processor and a display.

FIG. 1 is a block diagram illustrating a structure of a tomographic image processing apparatus 100a according to an embodiment.

The tomographic image processing apparatus 100a according to disclosed embodiments that is an apparatus for processing and displaying CT image data may be implemented as an electronic apparatus. For example, the tomographic image processing apparatus 100a may be implemented as any of various apparatuses including a processor and a display such as a general-purpose computer, a tablet PC, or a smart phone.

The tomographic image processing apparatus 100a according to an embodiment includes an image processor 110 and a display 120.

CT image data may be represented by CT numbers (or HUs). Hereinafter, a grayscale of the display 120 is referred to as a "display grayscale', and a grayscale value represented in a grayscale range of the display 120 is referred to as a 'display grayscale value'. The number of CT numbers refers to the number of different values that a CT number may have, and the number of display grayscale values refers to the number of different values that a display grayscale value may have. The number of display grayscale values may be referred to as the number of gray levels.

The image processor 110 receives CT image data, and performs predetermined processing. The image processor 110 sets two or more CT number ranges of interest for CT numbers of the CT image data, and maps the CT numbers of the CT image data to display grayscale values of the display 120.

The image processor 110 may be implemented as any of various combinations of at least one memory and at least one processor. For example, the memory may generate and delete a program module according to an operation of the image processor 110, and the processor may process operations of the program module.

The image processor 110 may respectively match display grayscale values to CT numbers, and may determine a corresponding relationship between the CT numbers and the display grayscale values. The matching of the display grayscale values to the CT numbers may be performed by using any of various methods such as a method of performing matching on each CT number, a method of adjusting a value and a gradient of a transfer graph, or a method of defining a lookup table.

According to an embodiment, the image processor 110 may convert the CT image data represented by the CT numbers into the display grayscale values according to a matching result, may generate image data for display, and may output the image data for display to the display 120.

According to an embodiment, when a width and a level of a CT number range of interest are set, the image processor 110 may match the CT numbers and the display grayscale values so that a ratio of the number of the display grayscale values to the number of the CT numbers in a CT number range included in the CT number range of interest is greater than that in a CT number range not included in the CT number range of interest. Also, the image processor 110 may match the CT numbers and the display grayscale values so that a graph showing a relationship between the CT numbers and the display grayscale values has a zero or positive gradient over an entire section, or has a zero or negative gradient over the entire section.

The display 120 displays the CT image data according to the matching result. According to an embodiment, the display 120 may receive the image data for display corresponding to the CT image data from the image processor 110, and may display the image data for display.

The display 120 includes a plurality of pixels, and displays image data. The display 120 may be implemented as, for example, a liquid-crystal display device, an organic electroluminescent device, an electrophoretic display device, or a cathode ray tube (CRT).

According to an embodiment, the image processor 110 may receive information about a display grayscale value range and the number of gray levels of the display 120 from the display 120, or may previously store the information in a predetermined storage medium.

Figure 2:
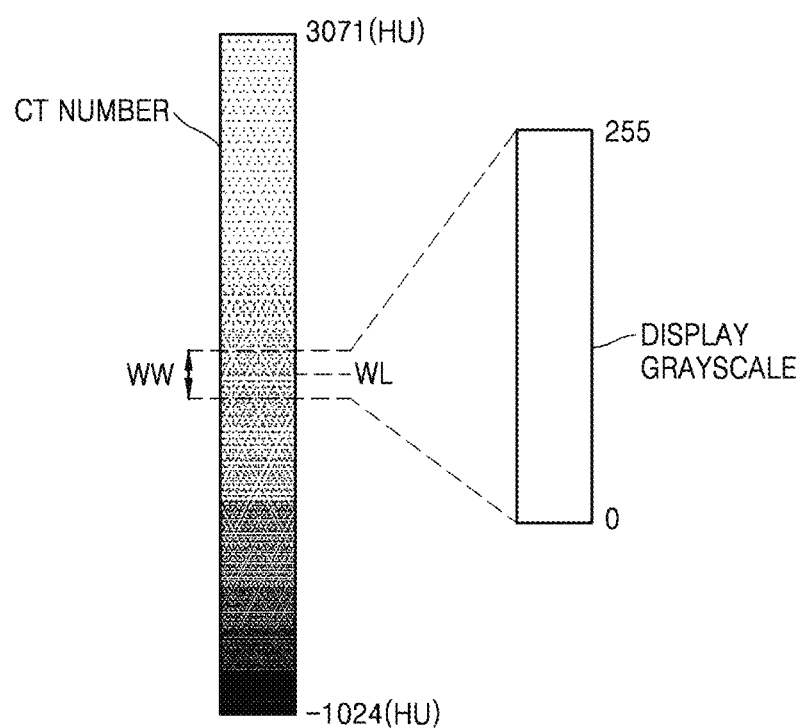
FIG. 2 is a diagram for explaining a computed tomography (CT) number and a display grayscale according to an embodiment.

FIG. 2 is a diagram for explaining a CT number and a display grayscale according to an embodiment.

CT image data is represented within a predetermined CT number range. For example, 12-bit CT image data may be represented by 4096 CT numbers, and a CT number of each pixel may be determined as an integer ranging from −1024 to 3071. A display grayscale of the display 120 may have grayscale values whose number is less than the number of the CT numbers of the CT image data. For example, when CT numbers are represented as 12-bit data, the display 120 is represented as 8-bit data, and the display 120 displays CT image data, since the CT numbers and display grayscale values are not matched to each other in a one-to-one manner, part of the CT image data may not be displayed it is full detail.

Due to a difference between the number of CT numbers and the number of display grayscales, when CT image data is displayed, a CT number range of interest of the CT numbers may be set. The CT number range of interest corresponds to a predetermined CT number range. The CT number range of interest may be defined by a window level WL and a window width WW. The window level WL that is a representative value of the CT numbers included in the CT number range of interest may be represented as a middle CT number of a CT number range included in the CT number range of interest. The window width WW indicates the number of the CT numbers included in the CT number range of interest. For example, the CT number range of interest may be defined by a window width of 700 and a window level of 1000.

Figure 3A:
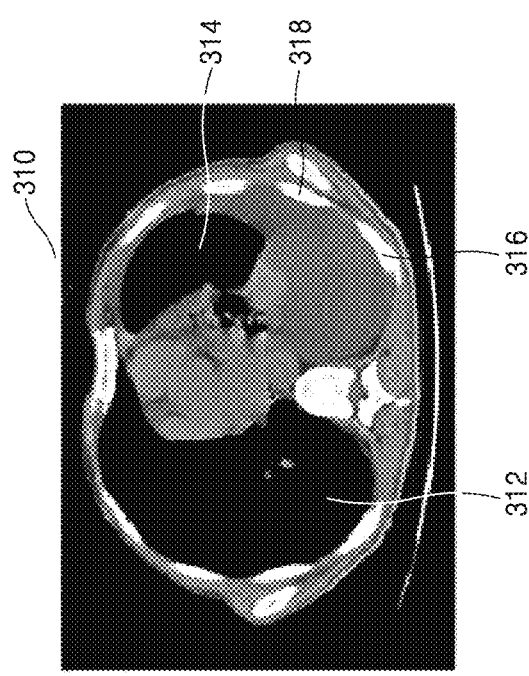
FIGS. 3A and 3B are diagrams illustrating a display image 310, a transfer graph 330, and a histogram 340, according to an embodiment.
Figure 3B:
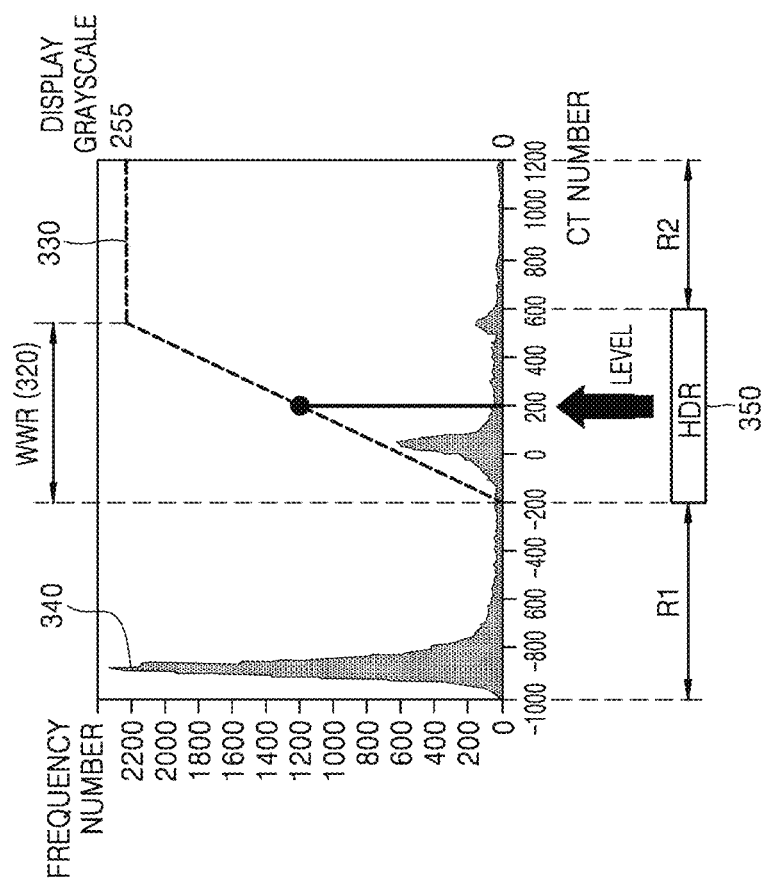

FIGS. 3A and 3B are diagrams illustrating a display image 310, a transfer graph (e.g., a transfer curve) 330, and a histogram 340 according to an embodiment.

According to an embodiment, a corresponding relationship between a CT number and a display grayscale value may be defined by using a transfer graph. For example, as shown in FIG. 3B, in a space where the horizontal axis represents a CT number and the vertical axis represents a display grayscale, the transfer graph 330 showing a relationship between the CT number and the display grayscale may be defined.

As shown in FIG. 3B, when a window width WW and a window level WL of a CT number range of interest 350 are defined, a gradient of the transfer graph 330 in a CT number range included in the CT number range of interest 350 may be set to be greater than that in a CT number range not included in the CT number range of interest 350. The image processor 110 may adjust a ratio between the number of CT numbers and the number of display grayscale values in a predetermined CT number range by adjusting a gradient of the transfer graph 330. Accordingly, CT numbers of CT image data in the CT number range included in the CT number range of interest 350 may be distinctively displayed so that different CT numbers correspond to different display grayscale values whereas the CT numbers of the CT image data in the CT number range not included in the CT number range of interest 350 may be displayed so that different CT numbers correspond to the same display grayscale value or a display grayscale value difference is less than a CT number difference. Accordingly, image data of the CT number range included in the CT number range of interest 350 shows a clear CT number difference whereas image data of the CT number range not included in the CT number range of interest 350 shows no or a small CT number difference. As such, a process where a display grayscale value difference is less than a CT number difference is referred to as grayscale compression.

FIG. 3A illustrates CT image data displayed according to the transfer graph 330 of FIG. 3B. The CT image data of FIG. 3A has a CT number distribution like the histogram 340 of FIG. 3B. Most of 8-bit display grayscale values are assigned in a CT number range included in the CT number range of interest 350 whereas only a limited number of display grayscale values are assigned in CT number ranges (e.g., R1 and R2) not included in the CT number range of interest 350, thereby leading to grayscale compression. Accordingly, part of the CT image data may be presented by a single grayscale even when there is a CT number difference. For example, although the CT image data of FIG. 3A is determined to have a high frequency number in a CT number range from −1000 to −700 of the histogram 340 as shown in FIG. 3B, CT numbers in the CT number range from −1000 to −700 are all expressed as a minimum display grayscale value of 0 and thus portions corresponding to the CT numbers are displayed as dark portions 312 and 314 in the display image 310. Also, although image data corresponding to the CT number range R2 exists in the histogram 340, CT numbers of the CT number range R2 are all expressed as a maximum display grayscale value of 255 and thus portions corresponding to the CT numbers are displayed as white portions 316 and 618 in the display image 310.

Figure 4:
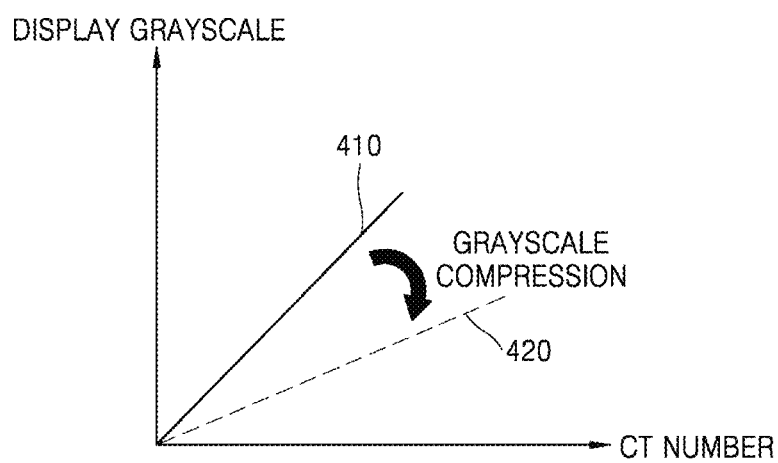
FIG. 4 is a diagram for explaining grayscale compression.

FIG. 4 is a diagram for explaining grayscale compression.

As described above, when CT numbers are not matched to display grayscale values in a one-to-one manner and are matched to display grayscale values whose number is less than the number of the CT numbers, grayscale compression occurs. As shown in FIG. 4, in a transfer graph where the horizontal axis represents a CT number and the vertical axis represents a display grayscale value, when a gradient is 1 (in a case 410), CT numbers and display grayscale values are matched in a one-to-one manner and all of the CT numbers are distinctively displayed. When a gradient is less than 1 (in a case 420), grayscale compression occurs and the number of display grayscale values is reduced to be less than the number of CT numbers.

According to an embodiment, the image processor 110 may not perform grayscale compression on a CT number range included in a CT number range of interest, and may perform grayscale compression on a CT number range not included in the CT number range of interest.

According to another embodiment, the image processor 110 may perform grayscale compression on both the CT number range included in the CT number range of interest and the CT number range not included in the CT number range of interest, and may set so that a gradient of a transfer graph in the CT number range included in the CT number range of interest is greater than a gradient in a transfer graph in the CT number range not included in the CT number range of interest.

Figure 5:
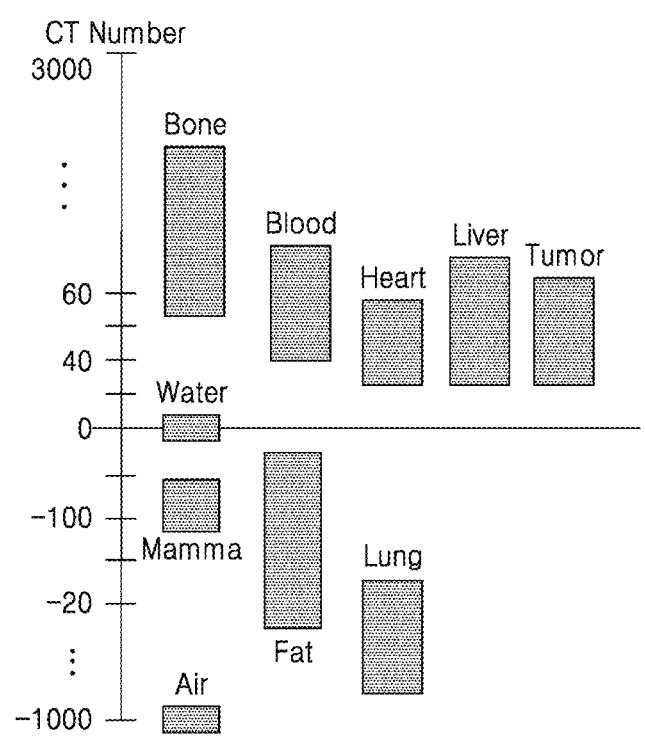
FIG. 5 is a diagram illustrating CT numbers of body tissue, organs, and materials, according to an embodiment.

FIG. 5 is a diagram illustrating CT numbers of body tissue, organs, and materials according to an embodiment.

A variable associated with CT image data may be referred to as a CT number. Body tissue, organs, and materials have their own CT numbers according to components and structures. As such, since body tissue, organs, and materials have their own CT numbers, parts in a CT image may be distinctively displayed, and a user may make a diagnosis by checking a state of an object by using the CT image.

Body tissue, organs, and materials may have CT numbers as shown in FIG. 5. First, air may have a CT number of about −1000, and water may have a CT number of about 0. A lung, fat, and a mamma having a high air content may each have a low CT number ranging from −1000 and 0. A bone, blood, the heart, the liver, and a tumor having a low air content and a high density may each have a CT number ranging from 0 to 3000. As such, since body tissue, organs, and materials have CT numbers with different ranges, it is preferable that when a diagnosis is made by using a CT image, CT image data is displayed by setting a CT number range of interest corresponding to a CT number range corresponding to body tissue, an organ, or a material of interest.

Figure 6A:
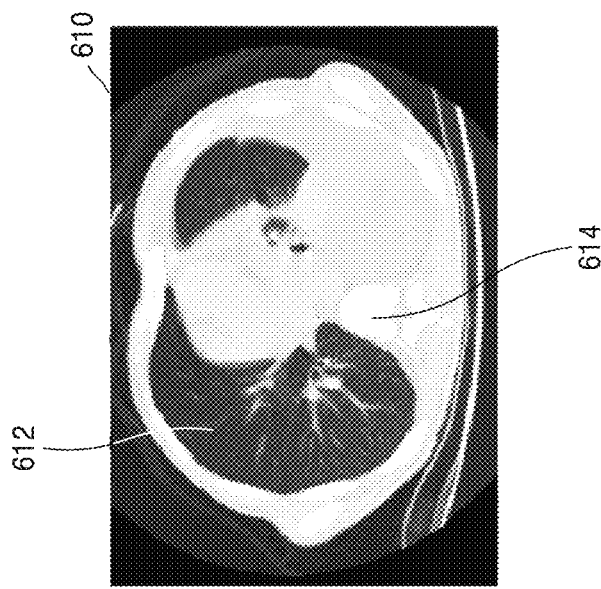
FIGS. 6A and 6B are diagrams illustrating a display image 610, transfer graphs 630 and 632, and a histogram 640, according to an embodiment.
Figure 6B:
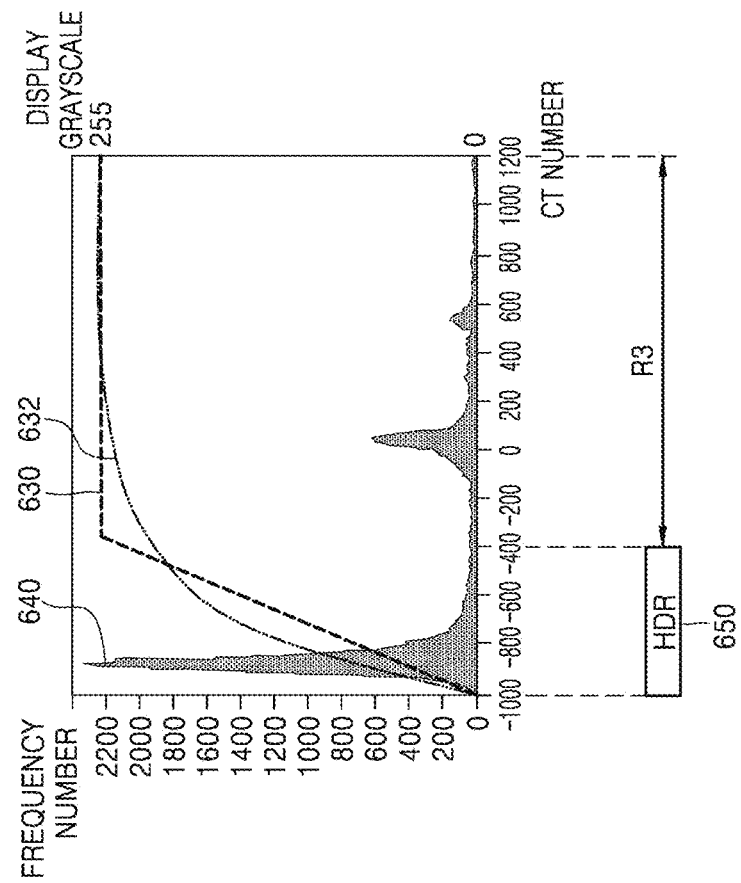

FIGS. 6A and 6B are diagrams illustrating a display image 610, transfer graphs 630 and 632, and a histogram 640 according to an embodiment.

According to an embodiment, a CT number range of interest 650 is set as a CT number range corresponding to a CT number range of a lung. For example, the CT number range of interest 650 may be set to have a window width of 600 and a window level of −700. Once the CT number range of interest 650 is set, the image processor 110 may display CT image data as the display image 610 of FIG. 6A by using the transfer graph 630 or 632 as shown in FIG. 6B. The transfer graph 630 or 632 of FIG. 6B has a high gradient in a CT number range corresponding to the CT number range of interest 650 so that a body part having a CT number corresponding to the CT number range of interest 650 may be displayed precisely. For example, the CT number range corresponding to the CT number range of interest 650 may correspond to the CT number range of the lung, and a region 612 corresponding to the lung may be precisely displayed on the display image 610 in a wide display grayscale value range. In contrast, a CT number range not included in the CT number range of interest 650 is represented by a limited number of grayscale values so that a region 614 may be displayed at almost the same brightness.

The transfer graph 630 or 632 may be represented as a linear graph 630 or a curve graph 632 according to embodiments.

Figure 7A:
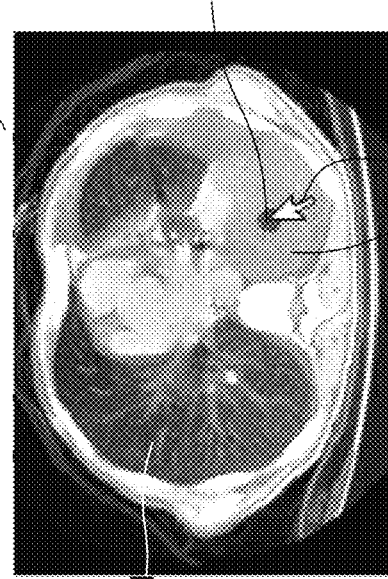
FIGS. 7A and 7B are diagrams illustrating a display image 710, transfer graphs 730 and 732, and a histogram 740, according to an embodiment.
Figure 7B:
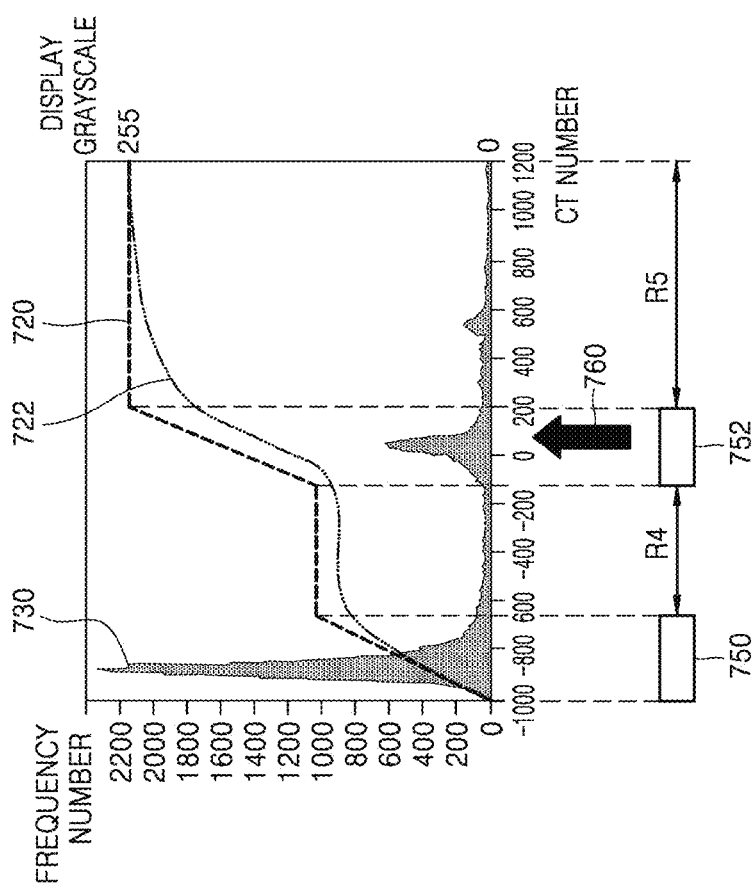

FIGS. 7A and 7B are diagrams illustrating a display image 710, transfer graphs 730 and 732, and a histogram 740 according to an embodiment.

According to an embodiment, the image processor 110 may set two or more CT number ranges of interest, and may set a transfer graph so that a gradient has a zero or positive value or a zero or negative value over an entire section of the transfer graph.

The two or more CT number ranges of interest may be set by using any of various methods. According to an embodiment, when a CT number range of interest 1 is set as an existing default range and a user sets a CT number range of interest 2, the CT number range of interest 1 and the CT number range of interest 2 are set. According to another embodiment, when there is no set CT number range of interest, the user may set the CT number range of interest 1 and the CT number range of interest 2.

The number of CT number ranges of interest may be set to 2 or more, for example, 2, 3, or 4, according to embodiments. According to an embodiment, when the maximum number of CT number ranges of interest is previously set, and the number already reaches the maximum number of CT number ranges of interest when the user is to add a CT number range of interest, a CT number range of interest that is the earliest set range may be removed and the CT number range of interest to be added by the user may be additionally set. For example, when the maximum number of CT number ranges of interest is 2 and a CT number range of interest 3 is to be additionally set by the user in a state where the CT number range of interest 1 and the CT number range of interest 2 are set, the CT number range of interest 1 that is set earlier than the CT number range of interest 2 may be removed and the CT number range of interest 3 may be added.

When a first CT number range of interest 750 and a second CT number range of interest 752 are set as shown in FIG. 7B, gradients of the transfer graphs 720 and 722 in CT number ranges corresponding to the first CT number range of interest 750 and the second CT number range of interest 752 are set to be greater than gradients of the transfer graphs 720 and 722 in CT number ranges R4 and R5 that are not set as CT number ranges of interest. In the transfer graphs 720 and 722, since a CT number difference is identifiably displayed on the display image 710 in the two CT number ranges respectively corresponding to the first CT number range of interest 750 and the second CT number range of interest 752, two or more body parts having different CT number levels may be identifiably displayed on the display image 710. For example, when the first CT number range of interest 750 corresponds to a CT number of a lung 712 and the second CT number range of interest 752 corresponds to a CT number of soft tissue 714, image data of the lung 712 and the soft tissue 714 may be identifiably displayed on one display image 710.

According to disclosed embodiments, when two or more CT number ranges whose frequency numbers are equal to or greater than a reference value exist as in the histogram 730 of FIG. 7B, the two or more CT number ranges may be identifiably displayed on the display image 710 by setting two or more CT number ranges of interest.

Also, according to disclosed embodiments, as shown in FIG. 7B, the transfer graphs 720 and 722 have a zero or positive gradient or a zero or positive gradient over an entire section. When a transfer graph as both a positive gradient and a negative gradient, grayscale inversion occurs in a display image. For example, when a CT number of a first pixel is 0, a CT number of a second pixel is 500, and a CT number of a third pixel is 1000, and display grayscale values are respectively 50, 30, and 60, a display grayscale value increases from 50 to 60 when a CT number increases from 0 to 1000 whereas a display grayscale value decreases from 50 to 30 when a CT number increases from 0 to 5000 which is grayscale inversion. Such grayscale inversion causes confusion and inconvenience to a user who reads CT image data. According to disclosed embodiments, since the transfer graphs 720 and 722 having two or more CT number ranges of interest 750 and 752 have a zero or positive gradient or a zero or negative gradient over the entire section, grayscale inversion does not occur. Accordingly, according to disclosed embodiments, without grayscale inversion, two or more body parts may be identifiably displayed in two or more CT number ranges of interest.

Figure 8:
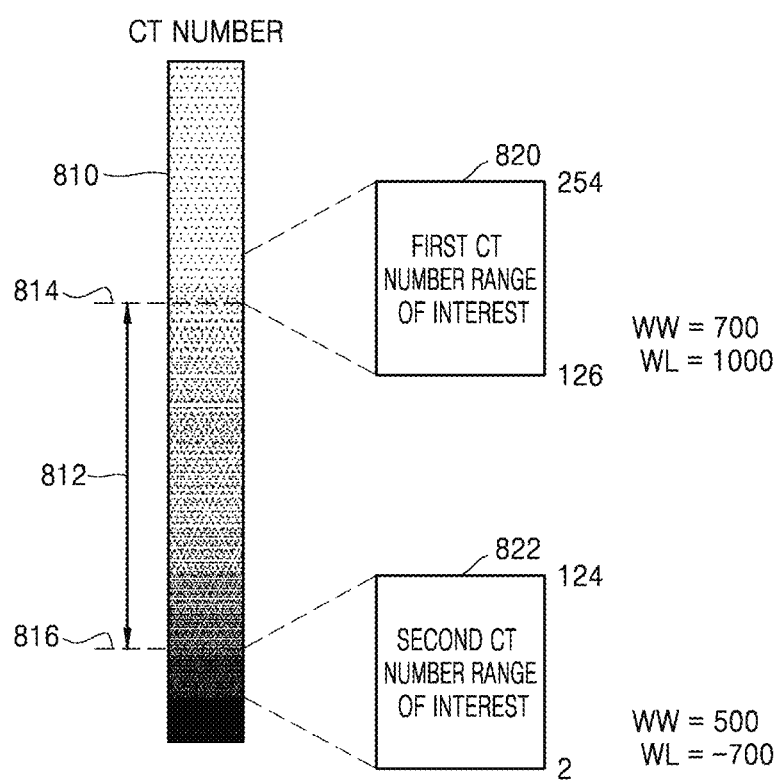
FIG. 8 is a diagram illustrating two or more CT number ranges of interest, according to an embodiment.

FIG. 8 is a diagram two or more CT number ranges of interest according to an embodiment.

According to an embodiment, two or more CT number ranges of interest, e.g., first and second CT number ranges of interest 820 and 822, may be set in two ranges in a CT number space 810. The first CT number range of interest 820 and the second CT number range of interest 822 may have a predetermined CT number difference 812. For example, a minimum CT number 814 of the first CT number range of interest 820 and a maximum CT number 816 of the second CT number range of interest 822 may have the predetermined CT number difference 812.

In one CT number range of interest, CT numbers may be continuous and display grayscale values may be continuous. For example, the first CT number range of interest 820 may correspond to CT numbers ranging from 650 to 1050 and display grayscale values ranging from 126 to 254, and the second CT number range of interest 822 may correspond to CT numbers ranging from −950 to −450 and display grayscale values ranging from 2 to 124.

Each CT number range of interest may be defined by a window width WW and a window level WL. For example, the first CT number range of interest 820 may be defined by a window width WW of 700 and a window level WL of 1000, and the second CT number range of interest 822 may be defined by a window width WW of 500 and a window level WL of −700.

According to an embodiment, the first CT number range of interest 820 may correspond to a CT number of a lung, and the second CT number range of interest 822 may correspond to a CT number of a bone. The lung has a low CT number of about −700. In contrast, the bone has a high CT number of about 1000. When the CT and surroundings are CT-scanned, bone tissue such as a rib or a spine is displayed along with the lung. Accordingly, when the first CT number range of interest 820 is set to correspond to the CT number of the lung and the second CT number range of interest 822 is set to correspond to the CT number of the bone, the lung and the bone may be distinctively displayed on one image. Also, a CT number difference in each of the lung and the bone is displayed on the display image.

According to an embodiment, CT image data may be CT image data obtained by using a contrast agent, and the first CT number range of interest 820 may be a CT number range of interest corresponding to a CT number of cancer tissue that absorbs the contrast agent and the second CT number range of interest may be a CT number range of interest corresponding to a CT number of soft tissue. The cancer tissue easily absorbs the contrast agent. Accordingly, when the contrast agent is injected into an object and then a CT scan is performed, the cancer tissue have absorbed the contrast agent has a very high CT number. In contrast, the soft tissue has a low CT number equal to or less than 0. Accordingly, when the first CT number range of interest 820 is set to correspond to the CT number of the cancer tissue that absorbs the contrast agent and the second CT number range of interest 822 is set to correspond to the CT number of the soft tissue, the cancer tissue and the soft tissue may be distinctively displayed on one screen. Also, a CT number difference in each of the cancer tissue and the soft tissue is displayed on a display image.

Figure 9:
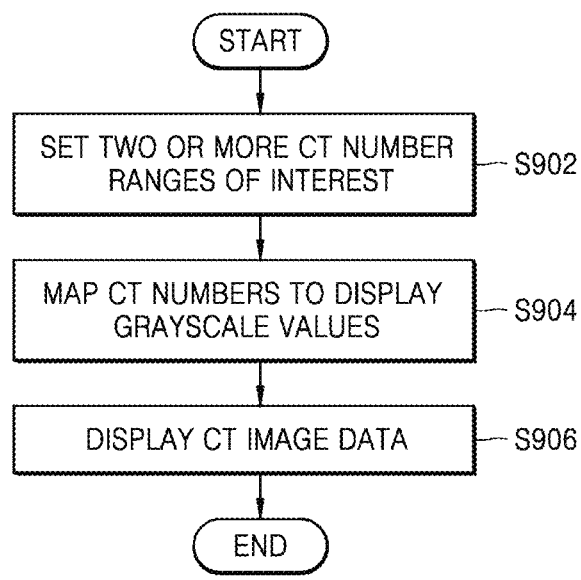
FIG. 9 is a flowchart illustrating a tomographic image processing method according to an embodiment.

FIG. 9 is a flowchart of a tomographic image processing method according to an embodiment.

Operations of the tomographic image processing method according to disclosed embodiments may be performed by an electronic apparatus including a processor for processing an image and a display. The following will be described on the assumption that a tomographic image processing apparatus 100 (hereinafter, 100 denotes any tomographic image processing apparatus of the present disclosure) performs the tomographic image processing method according to disclosed embodiments. Accordingly, the description made for the tomographic image processing apparatus 100 may apply to the tomographic image processing method, and the description made for the tomographic image processing method may apply to the tomographic image processing apparatus 100. Although the following is described on the assumption that the tomographic image processing method according to disclosed embodiments is performed by the tomographic image processing apparatus 100, embodiments are not limited thereto and the tomographic image processing method may be performed by any of various other electronic apparatuses.

In operation S902, the image processor 110 sets two or more CT number ranges of interest for CT numbers. The two or more CT number ranges of interest may be defined by a window width and a window level as described above.

Next, in operation S904, the image processor 110 maps the CT numbers to display grayscale values. For example, the image processor 110 may determine a transfer graph, and may map the CT numbers to the display grayscale values.

According to disclosed embodiments, a ratio of the number of the display grayscale values to the number of the CT numbers in a CT number range included in the two or more CT number ranges of interest is greater than that in a CT number range not included in the two or more CT number ranges of interest. For example, in the transfer graph, a gradient in the CT number range included in the two or more CT number ranges of interest is set to be greater than that in the CT number range not included in the two or more CT number ranges of interest.

Also, a graph showing a relationship between the CT numbers and the display grayscale values may have a zero or positive gradient, or a zero or negative gradient over an entire section.

Next, in operation S906, CT image data is displayed on the display 120 according to a matching result between the CT numbers and the display grayscale values. According to an embodiment, the image processor 110 generates image data for display by converting the CT numbers of the CT image data into the display grayscale values based on the matching result, and outputs the image data for display to the display 120. The display 120 displays the image data for display received from the image processor 110.

Figure 10:
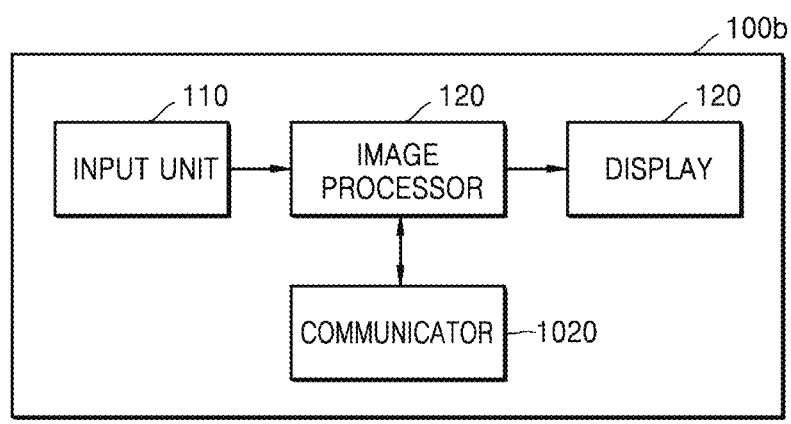
FIG. 10 is a block diagram illustrating a structure of a tomographic image processing apparatus 100b according to an embodiment.

FIG. 10 is a block diagram illustrating a structure of a tomographic image processing apparatus 100*b* according to an embodiment.

The tomographic image processing apparatus 100*b* according to an embodiment includes the image processor 110, the display 120, an input unit 1010, and a communicator 1020. The same description made for the image processor 110 and the display 120 with reference to FIG. 1 will not be given in FIG. 10. FIG. 10 will be described by focusing on a difference from an embodiment of FIG. 1.

The image processor 110 according to the present embodiment may set at least one from among two or more CT number ranges of interest based on a control signal or data input through the communicator 1020 or a user input received through the input unit 1010. According to embodiments, one or a combination of the input unit 1010 and the communicator 1020 may be provided in the tomographic image processing apparatus 100*b*.

The input unit 1010 receives a control signal or data from a user. The input unit 1010 may include, for example, a key, a track ball, a button, a touchscreen, a touch sensor, a touchpad, a mouse, a stylus pen, or a microphone, or a combination thereof. The input unit 1010 may receive various user inputs for controlling an operation of the tomographic image processing apparatus 100*b*. For example, the input unit 1010 may receive a user input for controlling an operation such as an imaging operation, a data producing operation, or a data transmitting/receiving operation. The image processor 110, or a separate controller (not shown) of the tomographic image processing apparatus 100 may operation in accordance with a user input received through the input unit 1010.

The input unit 1010 according to an embodiment may receive a user input that determines a window width and a window level of a CT number range of interest. For example, the user may input a control signal that adds a CT number range of interest, and then may determine a window width and a window level of the CT number range of interest through a graphical user interface (GUI) provided on the display 120.

The input unit 1010 according to an embodiment may receive a user input that designates at least one point of interest in CT image data. A process of receiving a user input will be described with reference to FIG. 7A. The user may select a point of interest by selecting one point 702 in displayed CT image data as shown in FIG. 7A. For example, in a state where a mouse pointer 716 is moved and located at the point of interest 702, the user may designate the point of interest 702 by clicking a mouse. Alternatively, the user may input a touch input that designates and selects the point of interest 702 by using a touchscreen or a touchpad. Alternatively, the user may move the mouse pointer 716 to the point of interest 702 by using a track ball, and may designate the point of interest 702 by inputting a selection signal by using a key or a button.

When the point of interest 702 is input, the image processor 110 sets at least one from among two or more CT number ranges of interest based on the designated point of interest 702. When a CT number range of interest that is previously set exists, the image processor 110 additionally sets a CT number range of interest based on the designated point of interest 702.

According to an embodiment, the image processor 110 determines a CT number of interest by using pixel values of pixels of a predetermined region around the point of interest 702. The predetermined region around the point of interest 702 may be set as a 5*5 pixel region or a 9*9 pixel region around a pixel corresponding to the point of interest 702. The image processor 110 may determine an average value, or an average value to which a weight is applied, of pixels included in the predetermined region as the CT number of interest. Alternatively, the image processor 110 may determine the CT number of interest based on a frequency number of pixel values of the pixels included in the predetermined region.

Also, the image processor 110 calculates the histogram 730 of the CT image data, and sets a CT number range in which the CT number of interest is included and that has a frequency number equal to or greater than a reference value in the histogram 730 as a CT number range of interest. For example, when the CT number of interest corresponds to a first CT number 760 shown in FIG. 7B, a CT number range including the first CT number 760 may be set as the CT number range of interest 752.

The CT number range of interest 752 may be set based on a frequency number of a histogram, or may be set based on a set window width and a set window level.

According to an embodiment, the CT number range of interest 752 may be set so that a frequency band of a histogram exceeds a reference level in a CT number range included in the CT number range of interest. For example, the CT number range of interest 752 may be set so that a frequency number of a histogram for each CT number included in the CT number range of interest exceeds a predetermined reference level.

According to an embodiment, the CT number of interest may be set by a window level of the CT number range of interest 752, and a window width of the CT number range of interest 752 may be set according to an additional user input.

Referring back to FIG. 10, other elements will now be described.

The communicator 1020 may communicate with an external apparatus through a network. The communicator 1020 may transmit/receive a control signal or data to/from the external apparatus. The external apparatus includes any of various electronic apparatuses such as a medical apparatus, a communication terminal, a tablet PC, a general-purpose PC, or a medical terminal.

A user input that may be received through the input unit 1010 may be received through the communicator 1020 according to embodiments. The communicator 1020 according to an embodiment may receive a control signal that adds a CT number range of interest from the external apparatus. Also, the communicator 1020 may receive a control signal that designates a window width and a window level of the CT number range of interest. When the control signal is received through the communicator 1020, the image processor 110 and the communicator 1020 may provide an interface through which a predetermined control signal may be input when the external apparatus is connected to the tomographic image processing apparatus 100*b*.

Figure 11:
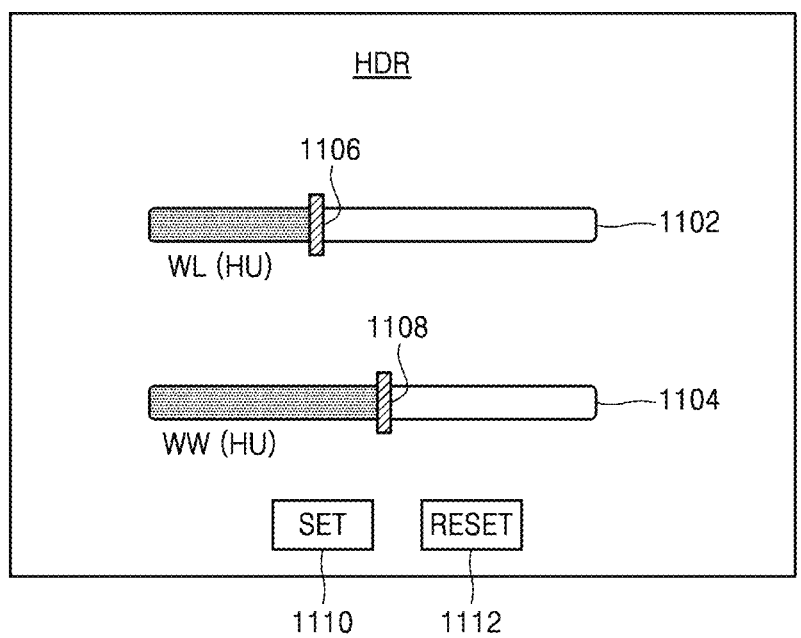
FIG. 11 is a diagram illustrating a graphical user interface (GUI) screen according to an embodiment.

FIG. 11 is a diagram illustrating a GUI screen according to an embodiment.

According to an embodiment, a GUI through which a user may input a window width WW and a window level WL may be provided. On a GUI screen according to an embodiment, a first bar 1102 indicating an adjustable range of the window level WL is displayed as shown in FIG. 11, and the window level WL may be adjusted by adjusting a position of a level control icon 1106 on the first bar 1102. Also, on the GUI screen according to an embodiment, a second bar 1104 indicating an adjustable range of the window width WW is displayed as shown in FIG. 11, and the window width WW may be adjusted by adjusting a position of a width control icon 1108 on the second bar 1104.

According to an embodiment, as positions of the level control icon 1106 and the width control icon 1108 are changed, information about a window level and a window width corresponding to current positions of the level and width control icons 1106 and 1108 may be displayed on the GUI. According to various embodiments, information about values corresponding to the current positions of the level and width control icons 1106 and 1108 may be displayed around a corresponding icon, or may be displayed around the first bar 1102 or the second bar 1104.

When the window width and the window level are completely set, the user may select a setting button 1110, and may apply a CT number range of interest setting value to the window width and the window level corresponding to the current positions of the level control icon 1106 and the width control icon 1108. Also, the user may set a reset 1112, and may set the window width and the widow level as predetermined default values.

According to another embodiment, the user may directly set a minimum CT number and a maximum CT number of a CT number range of interest. For example, the user may set the CT number range of interest by inputting −1000 as the minimum CT number and inputting −400 as the maximum CT number.

According to another embodiment, the user may set the CT number range of interest by setting a predetermined region on an axis representing a CT number. For example, the user may set the CT number range of interest by dragging a region corresponding to −1000 to −400 on the axis corresponding to CT numbers of an entire range or selecting a point corresponding to −1000 and a point corresponding to −400.

Figure 12:
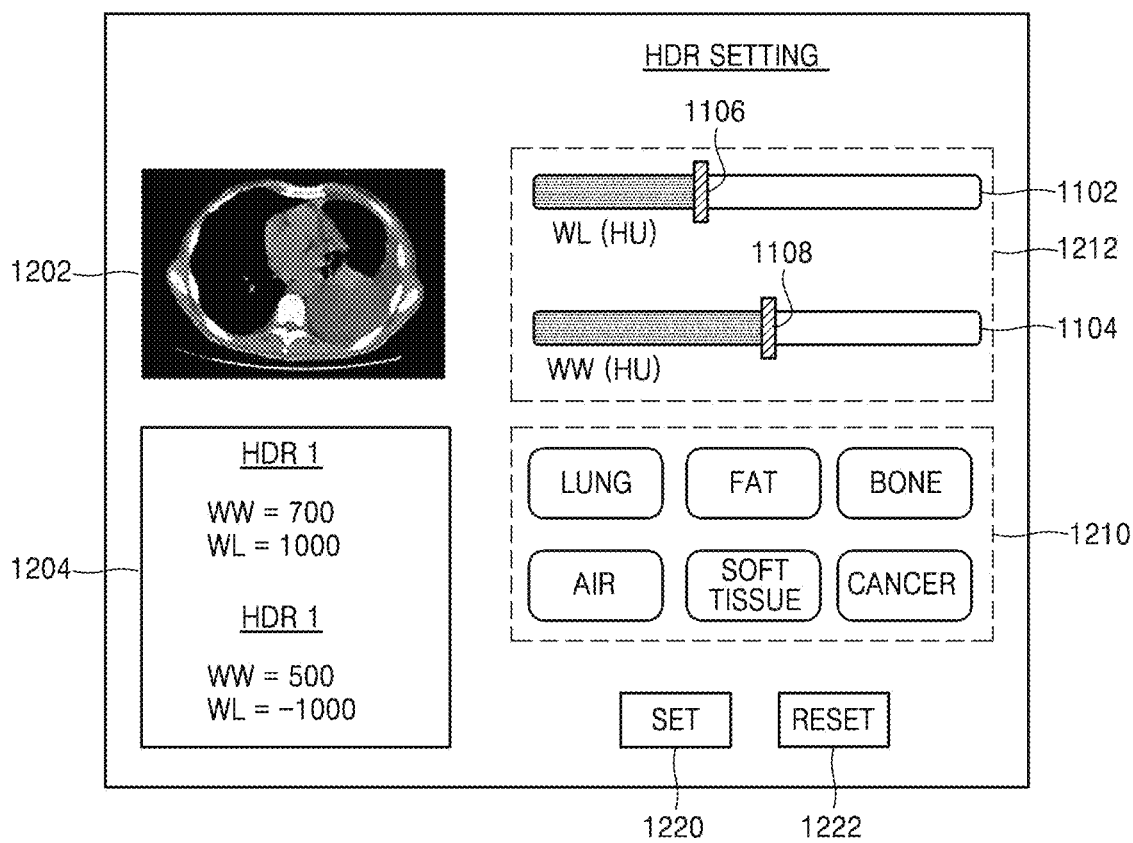
FIG. 12 is a diagram illustrating a GUI screen according to an embodiment.

FIG. 12 is a diagram illustrating a GUI screen according to an embodiment.

According to an embodiment, CT image data 1202, a CT number range of interest display area 1204 indicating information about a CT number range of interest that is current set, a CT number range of interest setting area 1212 for setting a window width and a window level, and a preset area 1210 for selecting a body part may be displayed on the GUI screen. An arrangement and a configuration of the GUI screen, parameter types, and candidate parameters may vary according to specific embodiments.

The CT image data 1202 displayed on the GUI screen may be an original image to which the CT number range of interest is not applied, or a display image to which the CT number range of interest displayed on the CT number range of interest display area 1204 is applied. According to embodiments, the original image and the display image to which the CT number range of interest is applied may be simultaneously displayed on the GUI screen. When the original image is displayed, the original image may be displayed in a grayscale compressed state at the same ratio for CT numbers of an entire range.

According to an embodiment, a GUI may provide a preview screen according to a value set by a user in the CT number range of interest setting area 1212 or a value set by the user in the preset area 1210. Accordingly, the user may receive a feedback on the GUI by inputting a predetermined setting value to the CT number range of interest setting area 1212 or the preset area 1210.

The CT number range of interest setting area 1212 may include the first bar 1102, the level control icon 1106, the second bar 1104, and the width control icon 1108 as described with reference to FIG. 11.

The preset area 1210 is a GUI area for setting a window width and a window level by selecting a body part or tissue. When one body part or tissue is selected on the preset area 1210, a CT number range corresponding to a CT number corresponding to the selected body part or tissue may be set as the CT number range of interest. For example, when the preset area 1210 displays selection buttons indicating a lung, fat, a bone, air, soft tissue, and cancer, and the user selects the lung, a CT number range (e.g., from −1000 to −400) corresponding to the lung is set as the CT number range of interest.

According to an embodiment, when a body part or tissue is selected in the preset area 1210, a window width and a window level that are previously set for the selected body part or tissue are set in the CT number range of interest setting area 1212. In detail, in accordance with the window width and the window level that are previously set for the selected body part or tissue in the preset area 1210, positions of the level control icon 1106 and the width control icon 1108 of the CT number range of interest setting area 1212 may be respectively moved on the first bar 1102 and the second bar 1104.

According to an embodiment, when a body part or tissue is selected in the preset area 1210, a new CT number range of interest may be set by a window width and a window level that are previously set for the selected body part or tissue, and information about the new CT number range of interest may be added to the CT number range of interest display area 1204. For example, when the user selects the lung, a CT number range of interest corresponding to a window width (e.g., 600) and a window level (e.g., −700) that are previously set for the lung may be newly set, and information about the newly set CT number range of interest may be displayed on the CT number range of interest display area 1204.

According to another embodiment, when a body part or tissue is selected in the preset area 1210, the level and width control icons 1106 and 1108 of the CT number range of interest setting area 1212 may be moved to correspond to a window width and a window level that are previously set for the selected body part or tissue, and when the user re-adjusts the window width and the window level in the CT number range of interest setting area 1212 and then selects a setting button 1220, the CT number range of interest may be set according to the window width and the window level that are set in the CT number range of interest setting area 1212. When a setting value selected in the preset area 1210 is displayed on the CT number range of interest setting area 1212, the user may directly set the setting value displayed on the CT number range of interest setting area 1212 as a CT number range of interest setting value, or may additionally adjust the setting value and may set the adjusted value as the CT number range of interest setting value.

According to an embodiment, when the user selects the lung in the preset area 1210, a first CT number range of interest corresponding to the lung may be set, and a second CT number range of interest corresponding to the bone may be automatically set. When the first CT number range of interest is set by selecting one body part and another body part is automatically selected, the body part that is automatically selected may be previously set.

According to an embodiment, when the user selects the cancer in the preset area 1210, a first CT number range of interest corresponding to the cancer may be set, and a second CT number range of interest corresponding to the soft tissue may be automatically set.

Figure 13:
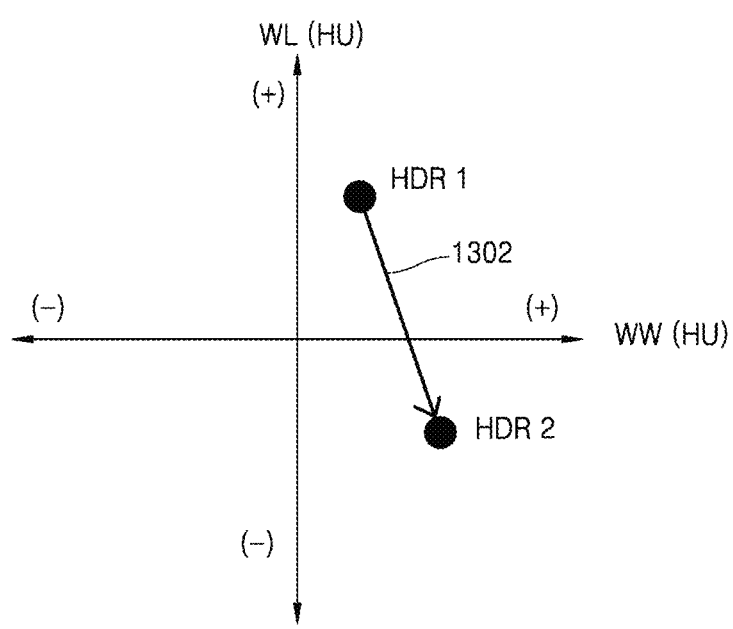
FIG. 13 is a diagram for explaining a GUI according to an embodiment.

FIG. 13 is a diagram for explaining a GUI according to an embodiment.

According to an embodiment, as shown in FIG. 13, a GUI that sets a window width WW and a window level WL on two intersecting axes may be provided. For example, a user may increase the window width WW by using a drag input in a (+) direction of the horizontal axis corresponding to the window width WW, and may reduce the window width WW by using a drag input in a (−) direction of the horizontal axis. Also, the user may increase the window level WL by using a drag input in a (+) direction of the vertical axis corresponding to the window level WL, and may reduce the window level WL by using a drag input in a (−) direction of the vertical axis. The GUI may include the horizontal axis corresponding to the window width WW (referred to as the horizontal axis WW) and the vertical axis corresponding to the window level WL (referred to as the vertical axis WL) shown in FIG. 13.

According to an embodiment, on a plane defined by the horizontal axis WW and the vertical axis WL displayed on a screen, a set CT number range of interest may be displayed. For example, on the plane defined by the horizontal axis WW and the vertical axis WL, a first CT number range of interest WW/WL 1 and a second CT number range of interest WW/WL 2 may be displayed. According to an embodiment, a window width and a window level of a CT number range of interest changed by a drag input of the user may be displayed on the plane. For example, when the window width is increased and the window level is reduced by a drag input of the user, a state where a CT number range of interest setting value is changed from the first CT number range of interest WW/WL 1 to the second CT number range of interest WW/WL 2 may be displayed on the GUI as shown in FIG. 13.

According to an embodiment, when the vertical axis and the horizontal axis are not displayed on a GUI screen and CT image data is displayed on the display 120, the image processor 110 may recognize a horizontal drag input as a drag input in a direction of the horizontal axis and may recognize a vertical drag input as a drag input in a direction of the vertical axis.

The tomographic image processing apparatus according to an embodiment may be implemented as a CT system.

Figure 14:
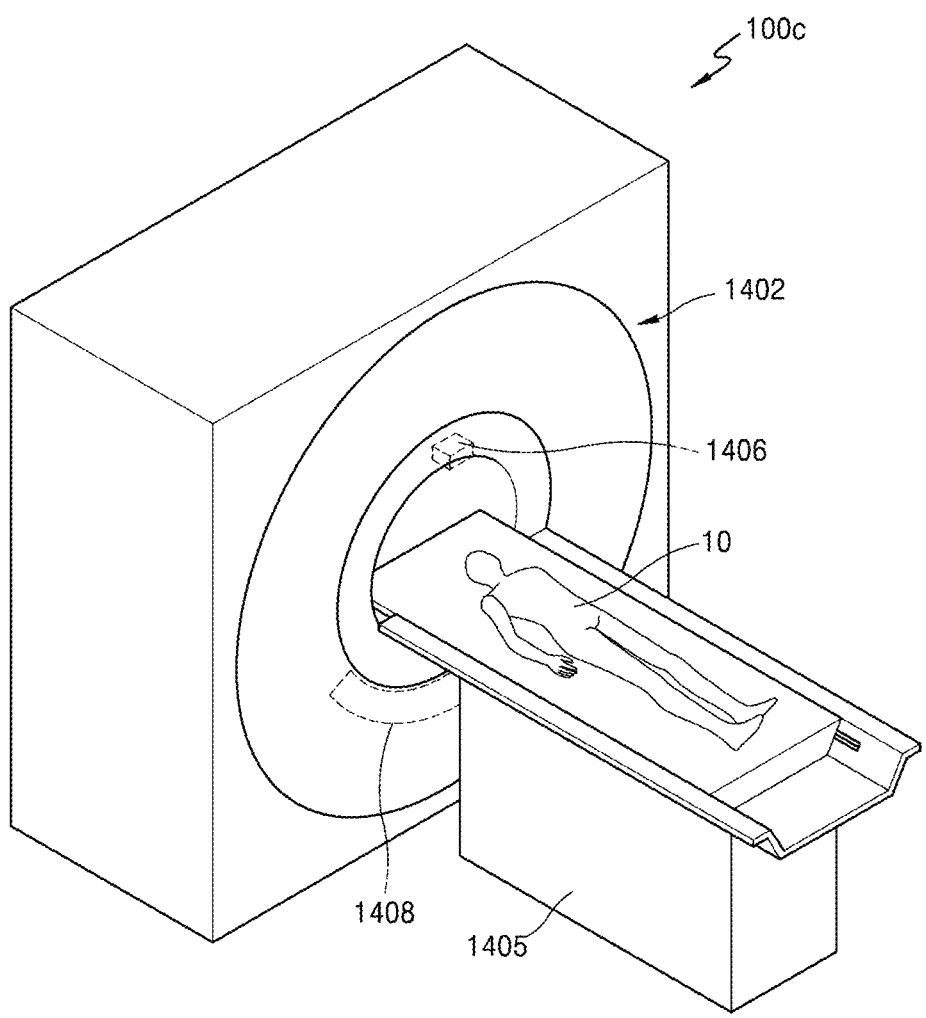
FIG. 14 is a view of a CT system 100c according to an embodiment.

FIG. 14 is a view of a CT system 100c according to an embodiment. Referring to FIG. 14, the CT system 100c may include a gantry 1402, a table 1405, an X-ray generator 1406, and an X-ray detector 1408.

The gantry 1402 may include the X-ray generator 1406 and the X-ray detector 1408.

An object 10 may be placed on the table 1405.

The table 1405 may be moved in a predetermined direction (e.g., at least one direction from among up, down, left, and right directions). Also, the table 1405 may be tilted or rotated by a predetermined angle in the predetermined direction.

Also, the gantry 1402 may also be tilted by a predetermined angle in a predetermined direction.

Figure 15:
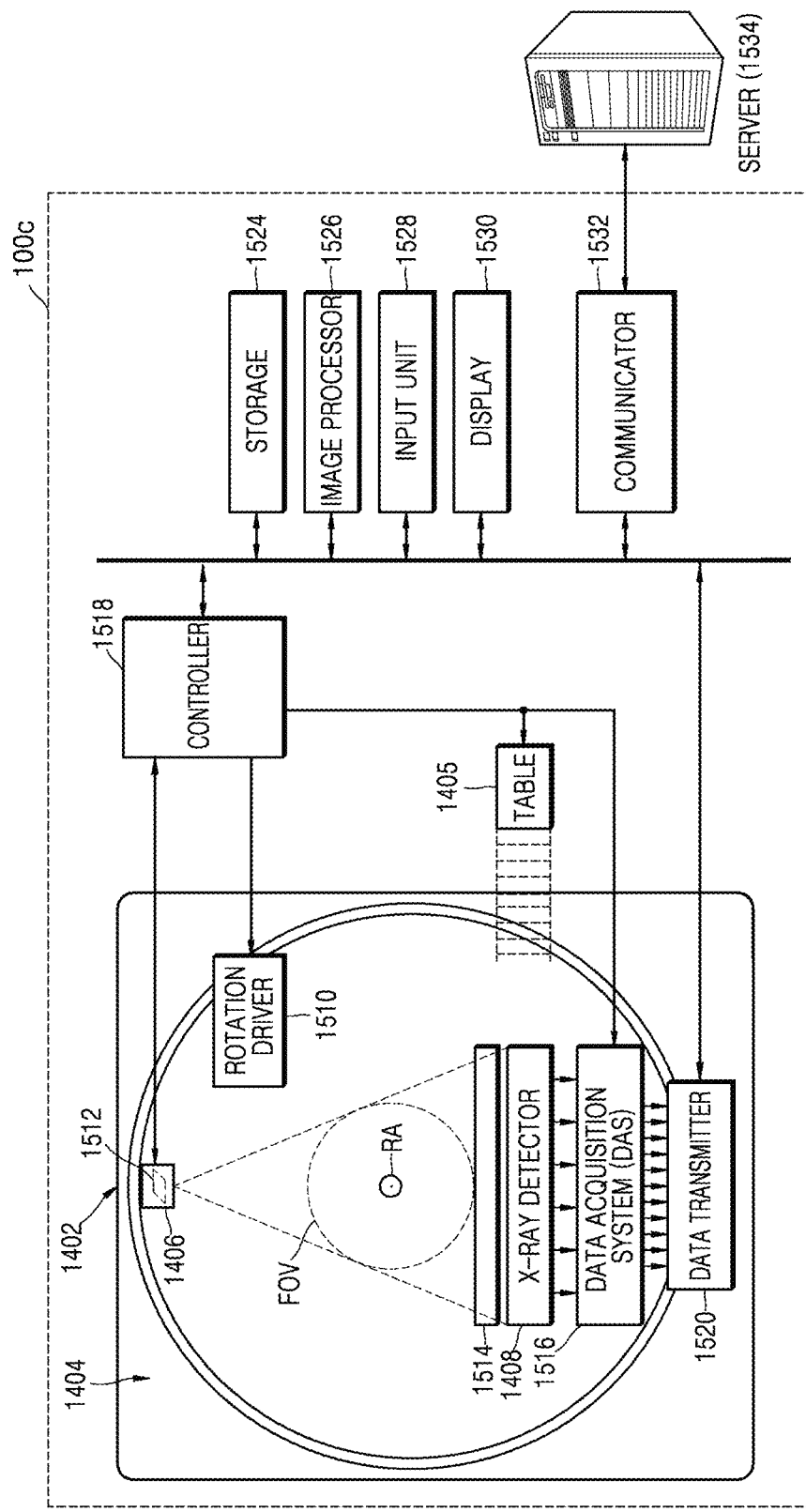
FIG. 15 is a diagram illustrating a structure of the CT system 100c according to an embodiment.

FIG. 15 is a diagram illustrating a structure of the CT system 100c according to an embodiment.

The CT system 100c according to an embodiment may include the gantry 1402, the table 1405, a controller 1518, a storage 1524, an image processor 1526, an input unit 1528, a display 1530, and a communicator 1532.

As described above, the object 10 may be placed on the table 1405. The table 1405 according to an embodiment of the present disclosure may move in a predetermined direction (e.g., at least one direction from among up, down, left, and right directions), and movement of the table 1405 may be controlled by the controller 1518.

The gantry 1402 according to an embodiment of the present disclosure may include a rotating frame 1504, the X-ray generator 1406, the X-ray detector 1408, a rotation driver 1510, a data acquisition system (DAS) 1516, and a data transmitter 1520.

The gantry 1402 according to an embodiment of the present disclosure may include the rotating frame 1504 having a loop shape and capable of rotating about a predetermined rotation axis (RA). Also, the rotating frame 1504 may have a disc shape.

The rotating frame 504 may include the X-ray generator 1406 and the X-ray detector facing each other to have a predetermined field of view (FOV). Also, the rotating frame 1504 may include an anti-scatter grid 1514. The anti-scatter grid 1514 may be located between the X-ray generator 1406 and the X-ray detector 1408.

In a medical imaging system, X-ray radiation that reaches a detector (or a photosensitive film) includes not only attenuated primary radiation that forms a valuable image but also scattered radiation that deteriorates the quality of an image. In order to transmit most of the primary radiation and attenuate the scattered radiation, the anti-scatter grid 1514 may be located between a patient and the detector (or the photosensitive film).

For example, the anti-scatter grid 1514 may be formed by alternately stacking lead foil strips and an interspace material such as a solid polymer material, a solid polymer, or a fiber composite material. However, a type of the anti-scatter grid 1514 is not limited thereto.

The rotating frame 1504 may receive a driving signal from the rotation driver 1510, and may rotate the X-ray generator 1406 and the X-ray detector 1408 at a predetermined rotation speed. The rotating frame 1504 may receive a driving signal and power from the rotation driver 1510 while the rotating frame 1504 contacts the rotation driver 1510 via a slip ring (not shown). Also, the rotating frame 1504 may receive a driving signal and power from the rotation driver 1510 through wireless communication.

The X-ray generator 1406 may receive a voltage and current from a power distribution unit (PDU) (not shown) via a slip ring (not shown) and then a high voltage generator (not shown), and may generate and emit X-rays. When the high voltage generator applies a predetermined voltage (hereinafter, referred to as a tube voltage), the X-ray generator 1406 may generate X-rays having a plurality of energy spectra that correspond to the tube voltage.

The X-rays generated by the X-ray generator 1406 may be emitted in a predetermined form by a collimator 112.

The X-ray detector 1408 may face the X-ray generator 1406. The X-ray detector 148 may include a plurality of X-ray detecting devices. Each of the plurality of X-ray detecting devices may establish a single channel, but embodiments are not limited thereto.

The X-ray detector 1408 may detect the X-rays generated by the X-ray generator 1406 and transmitted through the object 10, and may generate an electrical signal corresponding to an intensity of the detected X-rays.

The X-ray detector 1408 may include an indirect-type X-ray detector for detecting radiation after converting the radiation into light and a direct-type X-ray detector for detecting radiation after directly converting the radiation into electric charges. The indirect-type X-ray detector may use a scintillator. Also, the direct-type X-ray detector may use a photon counting detector. The DAS 1516 may be connected to the X-ray detector 1408. An electrical signal generated by the X-ray detector 1408 may be collected by the DAS 1516. The electrical signal generated by the X-ray detector 1408 may be collected by the DAS 1516 by wire or wirelessly. Also, the electrical signal generated by the X-ray detector 1408 may be applied through an amplifier (not shown) to an analog-to-digital converter (not shown).

Only some of a plurality of pieces of data collected by the X-ray detector 1408 may be provided to the image processor 1526 according to a slice thickness or the number of slices, or only some of the plurality of data may be selected by the image processor 1526.

Such a digital signal may be applied through the data transmitter 1520 to the image processor 1526. The digital signal may be transmitted through the data transmitter 1520 to the image processor 1526 by wire or wirelessly.

The controller 1518 according to an embodiment of the present embodiment may control an operation of each of modules of the CT system 100c. For example, the controller 1518 may control operations of the table 1405, the rotation driver 1510, the collimator 1512, the DAS 1516, the storage 1524, the image processor 1526, the input unit 15278, the display 1530, and the communicator 1532.

The image processor 1526 may receive data (e.g., raw data before processing) acquired by the DAS 1516 through the data transmitter 1520, and may perform pre-processing.

The pre-processing may include, for example, a process of correcting a sensitivity irregularity between channels and a process of correcting signal loss due to a rapid decrease in a signal strength or due to the presence of an X-ray absorbing material such as a metal.

Data output from the image processor 1526 may be referred to as raw data or projection data. The projection data may be stored in the storage 1524 along with imaging condition (e.g., a tube voltage and an imaging angle) during data acquisition.

The projection data may be a group of data values corresponding to the intensity of X-rays passing through the object 10. For convenience of explanation, a group of pieces of projection data simultaneously obtained from all channels at the same imaging angle is referred to as a projection data set.

The storage 1524 may include at least one storage medium from among a flash memory-type storage medium, a hard disk-type storage medium, a multimedia card microtype storage medium, a card-type memory (e.g., an SD or XD memory), a random-access memory (RAM), a static random-access memory (SRAM), a read-only memory (ROM), an electrically erasable programmable read-only memory (EEPROM), a programmable read-only memory (PROM), a magnetic memory, a magnetic disc, and an optical disc.

Also, the image processor 1526 may reconstruct a cross-sectional image of the object 10 by using the obtained projection data set. The cross-sectional image may be a 3D image. In other words, the image processor 1526 may generate a 3D image of the object 10 by using a cone beam reconstruction method or the like based on the obtained projection data set.

An external input for an X-ray CT imaging condition or an image processing condition may be input through the input unit 1528. For example, the X-ray CT imaging condition may include a plurality of tube voltages, a setting of energy values of a plurality of X-rays, a selection of an imaging protocol, a selection of an image reconstruction method, a setting of an FOV area, the number of slices, a slice thickness, and a setting of image post-processing parameters. Also, the image processing condition may include a resolution of an image, a setting of an attenuation coefficient of the image, and a setting of an image combining ratio.

The input unit 1528 may include a device for receiving a predetermined input from an external source. For example, the input unit 1528 may include a microphone, a keyboard, a mouse, a joystick, a touchpad, a touch pen, a voice recognition device, or a gesture recognition device.

The display 1530 may display an X-ray image reconstructed by the image processor 1526.

Exchanges of data and power among the above elements may be performed by using at least one of wired communication, wireless communication, and optical communication.

The communicator 1532 may communicate with an external apparatus or an external medical apparatus through a server 1534, which will be described with reference to FIG. 16.

Figure 16:
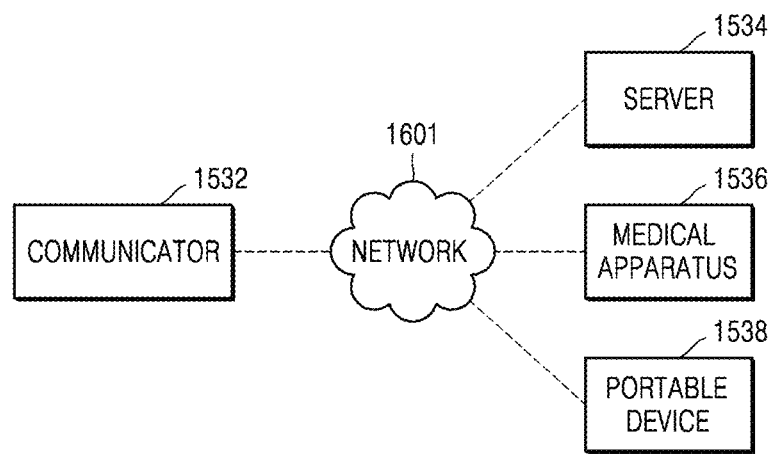
FIG. 16 is a block diagram illustrating a configuration of a communicator.

FIG. 16 is a block diagram illustrating a configuration of the communicator 1532.

The communicator 1532 may be connected to a network 301 by wire or wirelessly and may communicate with the server 1534, a medical apparatus 1536, or a portable device 1538. The communicator 1532 may transmit/receive data to/from a hospital server or other medical apparatuses in a hospital connected via a picture archiving and communication system (PACS).

Also, the communicator 1532 may communicate data with the portable device 1538 according to the digital imaging and communications in medicine (DICOM) standard.

The communicator 1532 may transmit/receive data related to diagnosing the object 10 through the network 1601. Also, the communicator 1532 may transmit/receive a medical image obtained by the medical apparatus 1536 such as a magnetic resonance imaging (MRI) apparatus or an X-ray apparatus.

Furthermore, the communicator 1532 may receive a diagnosis history or a medical treatment schedule about a patient from the server 15345 and may use the diagnosis history or the medical treatment schedule to diagnose the patient. Also, the communicator 1532 may communicate data not only with the medical apparatus 1536 or the server 1534 in a hospital but also with the portable device 1538 of a user or patient.

Also, information about a device error and a quality control status may be transmitted to a system manager or a service manager through the network 1601 and a feedback regarding the information may be received.

The image processor 1526 of FIG. 15 may correspond to the image processor 110 of FIGS. 1 and 10. The display 1530 of FIG. 15 may correspond to the display 120 of FIGS. 1 and 10. The input unit 1528 of FIG. 15 may correspond to the input unit 1010 of FIG. 10. The communicator 1532 of FIG. 15 may correspond to the communicator 1020 of FIG. 10.

The afore-described embodiments of the present disclosure may be implemented as a computer-executable program, and may be executed by a general-purpose computer that runs the program by using a computer-readable recording medium.

Examples of the computer-readable recording medium include magnetic storage media (e.g., ROMs, floppy disks, or hard disks), optical recording media (e.g., CD-ROMs, or DVDs), and carrier waves (e.g., data transmission through the Internet).

While the present disclosure has been particularly shown and described with reference to embodiments thereof, it will be understood by one of ordinary skill in the art that various changes in form and detail may be made therein without departing from the spirit and scope of the present disclosure as defined by the following claims. The embodiments should be considered in a descriptive sense only and not for purposes of limitation.

The invention claimed is:

1. A tomographic image processing apparatus comprising:
an image processor configured to set two or more computed tomography (CT) number ranges of interest defined by a window level and a window width for CT numbers of CT image data, and map the CT numbers to display grayscale values of a display; and
the display configured to display the CT image data according to a mapping result,
wherein a gradient of a graph showing a relationship between the CT numbers and the display grayscale values in a CT number range included in the two or more CT number ranges of interest is greater than a gradient in a CT number range not included in the two or more CT number ranges of interest,
wherein the graph showing the relationship between the CT numbers and the display grayscale values has a zero or positive gradient over an entire section, or has a zero or negative gradient over the entire section.

2. The tomographic image processing apparatus of claim 1, further comprising an input unit configured to receive a user input that designates at least one point of interest in the CT image data,
wherein the image processor is further configured to set at least one from among the two or more CT number ranges of interest based on the user input.

3. The tomographic image processing apparatus of claim 2, wherein the image processor is further configured to obtain a histogram of the CT numbers of the CT image data, determine a CT number of interest corresponding to a pixel value of a pixel region comprising a pixel corresponding to the at least one point of interest, and set a CT number range, which includes the CT number of interest and has a frequency number equal to or greater than a reference value in the histogram, as at least one from among the two or more CT number ranges of interest.

4. The tomographic image processing apparatus of claim 1, further comprising an input unit configured to receive a user input that designates a body part,
wherein the image processor is further configured to determine a CT number range corresponding to the body part designated by the user input, and set the determined CT number range as at least one from among the two or more CT number ranges of interest.

5. The tomographic image processing apparatus of claim 1, further comprising an input unit configured to receive a user input that designates a CT number or a CT number range,
wherein the image processor is further configured to set at least one from among the two or more CT number ranges of interest based on the CT number or the CT number range designated by the user input.

6. The tomographic image processing apparatus of claim 1, wherein a ratio of a number of display grayscale values to a number of CT numbers in the two or more CT number ranges of interest is 1, and
a ratio of a number of display grayscale values to a number of CT numbers in the CT number range not included in the two or more CT number ranges of interest is less than 1.

7. The tomographic image processing apparatus of claim 1, wherein a number of the CT numbers is greater than a number of the display grayscale values of the display.

8. The tomographic image processing apparatus of claim 1, wherein the two or more CT number ranges of interest comprise a first CT number range of interest and a second CT number range of interest,
wherein the first CT number range of interest has a window level corresponding to a lung, and the second CT number range of interest has a window level corresponding to a bone.

9. The tomographic image processing apparatus of claim 1, wherein the two or more CT number ranges of interest comprise a first CT number range of interest and a second CT number range of interest,
wherein the CT image data is CT image data obtained by CT imaging using a contrast agent,
wherein the first CT number range of interest has a window level corresponding to cancer tissue that absorbs the contrast agent, and the second CT number range of interest has a window level corresponding to soft tissue.

10. A tomographic image processing method comprising:
setting two or more computed tomography (CT) number ranges of interest defined by a window level and a window width for CT numbers of CT image data;
mapping the CT numbers to display grayscale values of a display; and
displaying the CT image data according to a mapping result,
wherein a gradient of a graph showing a relationship between the CT numbers and the display grayscale values in a CT number range included in the two or more CT number ranges of interest is greater than a gradient in a CT number range not included in the two or more CT number ranges of interest,
wherein the graph showing the relationship between the CT numbers and the display grayscale values has a zero or positive gradient over an entire section, or has a zero or negative value over the entire section.

11. The tomographic image processing method of claim 10, further comprising:
   receiving a user input that designates at least one point of interest in the CT image data; and
   setting at least one from among the two or more CT number ranges of interest based on the user input.

12. The tomographic image processing method of claim 11, further comprising:
   obtaining a histogram of the CT numbers of the CT image data;
   determining a CT number of interest corresponding to a pixel value of a pixel region comprising a pixel corresponding to the at least one point of interest; and
   setting a CT number range, which includes the CT number of interest and has a frequency number equal to or greater than a reference value in the histogram, as at least one from among the two or more CT number ranges of interest.

13. The tomographic image processing method of claim 10, further comprising:
   receiving a user input that designates a body part;
   determining a CT number range corresponding to the body part designated by the user input; and
   setting the determined CT number range as at least one from among the two or more CT number ranges of interest.

14. The tomographic image processing method of claim 10, further comprising:
   receiving a user input that designates a CT number or a CT number range; and
   setting at least one from among the two or more CT number ranges of interest, based on the CT number or the CT number range designated by the user input.

15. A computer-readable recording medium storing program code for executing the tomographic image processing method of claim 10.

* * * * *